US009005255B2

(12) United States Patent
Lewis et al.

(10) Patent No.: US 9,005,255 B2
(45) Date of Patent: Apr. 14, 2015

(54) ORTHOPEDIC COMPRESSION PLATE

(75) Inventors: Derek S. Lewis, Copley, OH (US);
Elizabeth Altenau, Cleveland, OH (US);
Gordon Bennett, Akron, OH (US);
Bryan D. Den Hartog, Rapid City, SD
(US); Jackson R. Heavener,
Wadsworth, OH (US); Jeffrey Johnson,
Chesterfield, MO (US); David B. Kay,
Akron, OH (US); Brian Hockett, Parma,
OH (US)

(73) Assignee: Orthohelix Surgical Designs, Inc.,
Medina, OH (US)

( * ) Notice: Subject to any disclaimer, the term of this
patent is extended or adjusted under 35
U.S.C. 154(b) by 96 days.

(21) Appl. No.: 13/372,902

(22) Filed: Feb. 14, 2012

(65) Prior Publication Data

US 2012/0209334 A1 Aug. 16, 2012

Related U.S. Application Data

(60) Provisional application No. 61/463,323, filed on Feb. 15, 2011, provisional application No. 61/580,680, filed on Dec. 28, 2011.

(51) Int. Cl.
*A61B 17/88* (2006.01)
*A61B 17/66* (2006.01)
*A61B 17/80* (2006.01)

(52) U.S. Cl.
CPC ......... *A61B 17/8061* (2013.01); *A61B 17/8014* (2013.01); *A61B 17/8095* (2013.01)

(58) Field of Classification Search
USPC ...................... 606/88, 82, 282, 281, 286, 291
See application file for complete search history.

(56) References Cited

U.S. PATENT DOCUMENTS

| 5,087,260 | A * | 2/1992 | Fixel .............................. 606/65 |
| 5,534,027 | A * | 7/1996 | Hodorek ..................... 128/898 |
| 5,667,510 | A * | 9/1997 | Combs ........................ 606/86 R |
| 5,693,055 | A * | 12/1997 | Zahiri et al. .................. 606/305 |
| 7,128,744 | B2 * | 10/2006 | Weaver et al. ................ 606/280 |
| 8,182,484 | B2 * | 5/2012 | Grant et al. .................... 606/66 |
| 8,187,276 | B1 * | 5/2012 | Zahiri et al. .................... 606/65 |
| 8,231,625 | B2 * | 7/2012 | Graham et al. ................ 606/71 |
| 8,556,946 | B2 * | 10/2013 | Prandi et al. ................. 606/286 |
| 8,617,224 | B2 * | 12/2013 | Kozak et al. ................. 606/290 |
| 2002/0045896 | A1 | 4/2002 | Michelson |
| 2004/0143266 | A1 | 7/2004 | Kozak et al. |
| 2005/0171544 | A1 | 8/2005 | Falkner, Jr. |
| 2008/0015593 | A1 * | 1/2008 | Pfefferle et al. ................ 606/69 |
| 2009/0036931 | A1 * | 2/2009 | Pech et al. .................... 606/280 |
| 2009/0210010 | A1 | 8/2009 | Strnad et al. |
| 2009/0210011 | A1 | 8/2009 | Den Hartog |
| 2010/0125300 | A1 | 5/2010 | Blitz et al. |
| 2010/0274293 | A1 | 10/2010 | Terrill et al. |
| 2011/0009866 | A1 * | 1/2011 | Johnson et al. ................ 606/70 |
| 2011/0098757 | A1 * | 4/2011 | Schelling ..................... 606/324 |
| 2011/0295324 | A1 | 12/2011 | Donley |

* cited by examiner

*Primary Examiner* — David Bates
(74) *Attorney, Agent, or Firm* — Hudak, Shunk & Farine Co. LPA

(57) ABSTRACT

An orthopedic plate has a first end including a locking screw hole that receives a locking screw and spaced from that hole is a compression housing that extends from the bone-facing side of the plate and which receives a compression screw that forms an angle of from about 10° to about 70° with a longitudinal axis of the plate. In a further embodiment, the plate also includes a second end with a chamfer for insertion of the plate into bone, and in a still further embodiment, the plate is an MTP plate.

17 Claims, 12 Drawing Sheets

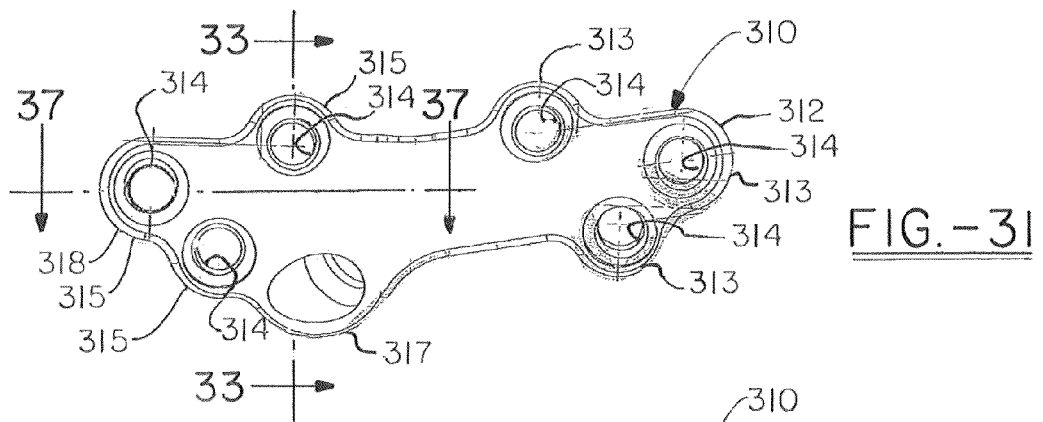
FIG.-31
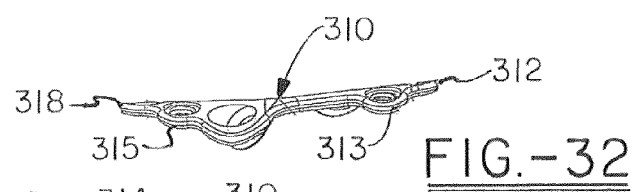
FIG.-32
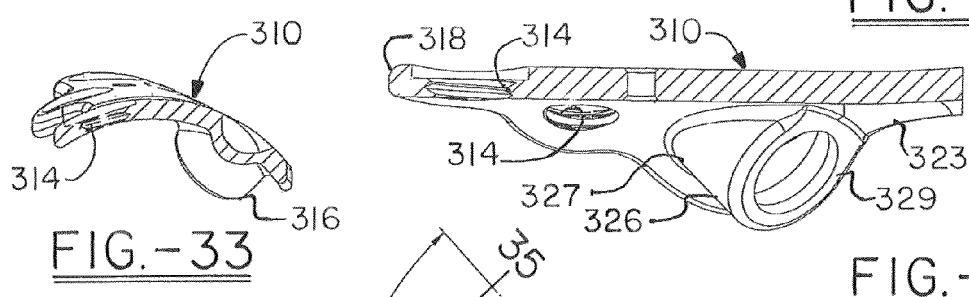
FIG.-33  FIG.-37
FIG.-34
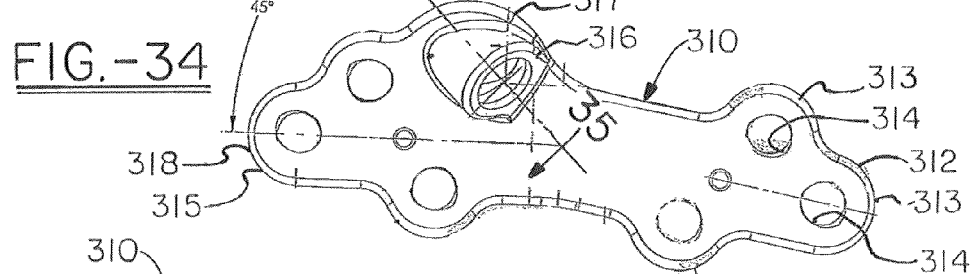
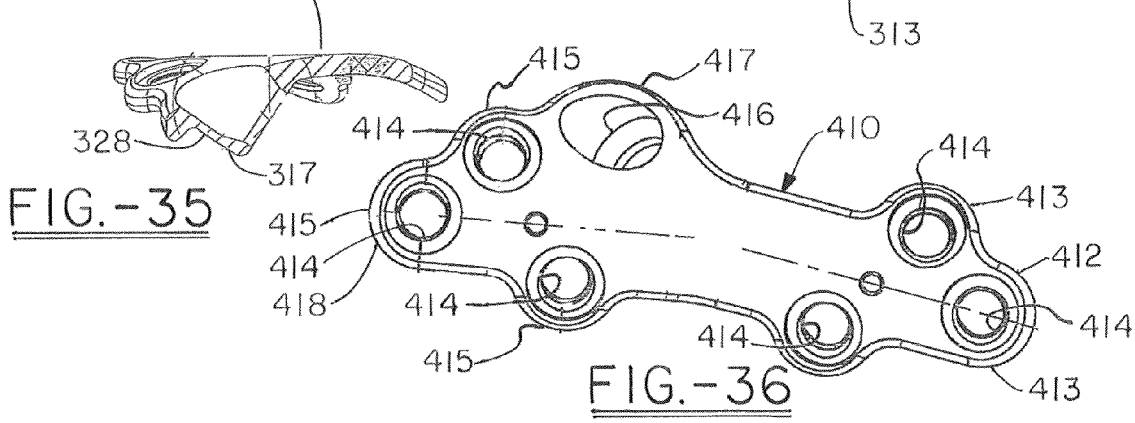
FIG.-35  FIG.-36

ORTHOPEDIC COMPRESSION PLATE

CROSS REFERENCE

This application claims the benefit of priority under 35 U.S.C. §119 of U.S. Provisional Application Ser. No. 61/463,323, filed on Feb. 15, 2011 and U.S. Provisional Application Ser. No. 61/580,680, filed on Dec. 28, 2011, herein fully incorporated by reference.

FIELD OF THE INVENTION

The present invention relates to an orthopedic plated which is configured to increase compression at a bone interface, in particular to stabilize bones or bone fragments relative to each other such as to cause fusion. Specific embodiments and methods of fixation are presented for fixation of the bones of the foot including, for example, stabilization of a fracture, dislocation or reconstruction of a deformity such as use in osteotomies and bunionectomies. The invention also applies to fusion procedures in other areas of the body, including the wrist or hand.

BACKGROUND OF THE INVENTION

The feet and the hands both include numerous bones and joints that cooperate together to define quintessential human movement. They are sophisticated, delicate and altogether elegant in function and design. Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body. The hand forms a cognate to the foot with 27 bones within the hand and wrist. There are eight small bones within the wrist called the carpals, which join with the radius and the ulna to form the wrist joint. The carpals connect with the five metacarpals to form the palm of the hand, which terminate in the rays (i.e., the thumb and fingers) formed by the phalanges. The three phalanges in each finger are separated by two joints, called interphalangeal joints (IP joints). The one closest to the MCP joint (knuckle) is called the proximal IP joint (PIP joint). The joint near the end of the finger is called the distal IP joint (DIP joint). The thumb only has one IP joint between the two thumb phalanges. The IP joints of the digits also work like hinges when you bend and straighten your fingers and thumb.

Similarly, the forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The forefoot balances pressure on the ball of the foot and bears a substantial amount of the body weight.

The bones of the midfoot from medial to lateral are the $1^{st}$ through $3^{rd}$ cuneiform, the cuboid, and the crescent shaped navicular bone posterior to the cuneiforms, which also forms a joint with the talus that forms the basis for the ankle joint at the hinged intersection of the tibia, the fibula, and the foot. The five tarsal bones of the midfoot act together form a lateral arch and a longitudinal arch, which help to absorb shock. The plantar fascia (arch ligament) underlays the bones of the midfoot and along with muscles, forms a connection between the forefoot and the hindfoot. The toes and their associated midfoot bones form the first through fifth rays beginning with the great toe as the first ray. The bones which form the palmate portion of the hand are: the scaphoid, the lunate, the triquetrum, the pisiform, the trapezium, the trapezoid, the capitate, and the hamate, which act in concert to allow the opposition of the thumb with each of the fingers and to permit the uniquely human ability to manipulate objects.

The hindfoot is composed of three joints (subtalar, calcaneocuboid & talonavicular) and links the midfoot to the ankle. The heel bone (or "calcaneus") projects posteriorly to the talus and forms a lever arm to activate the hinged action of the foot so as to allow propulsion of the entire body from this joint. The calcaneus is joined to the talus at the subtalar joint. The mid-foot is often the subject of trauma, such as results from falls, vehicle, crashes and dropped objects. These accidents often result in severe fractures and/or dislocations. In addition, there are several conditions which result from congenital deformation or which arise as a result of repeated use type injuries. Surgical intervention that includes surgical sectioning of bone or an "osteotomy" is often used to restructure the bones as a treatment for such conditions, for example, the bunionectomy. The present invention is likewise useful for conditions of the hand that result from prior trauma, surgical intervention or defects from birth or that develop with age (such as rheumatoid arthritis).

Examples of some of the other procedures with which the present invention could be used include hallus valgus and hallus rigidus corrections. Other applications which could use the present invention include first and fifth metatarsal chevrons, translational osteotomies, closing wedge osteotomies, pediatric femoral osteotomies, metacarpal and calcaneal rotational osteotomies, intrarticular osteotomies and hand and wrist realignment osteotomies. Specific surgical techniques are discussed for the use of an embodiment of the invention designed for use in bunionectomies.

Typical surgical treatment of the foot or hand re-establishes a normal anatomy while the fractured bones mend. In some cases, fusion of a joint may be necessary, for example, where arthritis arises in a patient due to use injuries, poor bone or prior unsuccessful surgeries. One current surgical treatment of these conditions requires that pins, wires and/or screws be inserted to stabilize the bones and joints and hold them in place until healing is complete. For example, a pin or screw may be introduced medially into the internal cuneiform and through the base of the second metatarsal bone. While the use of k-wires, pins, and screws may provide acceptable results for younger and more plastic patients, these methods of fixation are not always satisfactory.

SUMMARY OF THE INVENTION

In accordance with the present invention an orthopedic plate is provided that achieves improved compression through the use of a screw that is situated with its axis obliquely to the spine, of the plate (i.e. to the longitudinal axis of the plate taken at the opening of the compression opening of the plate). The screw is received in a housing which includes an opening in the top surface of the plate and a shroud which extends from the bottom surface of the plate so as to define a pocket on the bottom of the plate that captures the screw at a variable orientation. The housing extends through the plate to accommodate the entire diameter of the head of the screw. Thus, the screw head does not project beyond the top surface of the plate when the screw is fully seated in the housing. (By "top" it is meant herein the exterior facing surface, which is opposite the bone-facing surface, of the plate of the plate when the plate is in position on the bone. It is understood that the orientation relative to the ground is dependent on the orientation of the plate in space, and therefore that is not relevant in determining what is "top" in this case). The housing also includes ah opening on the bottom of the plate through which the screw extends and which is smaller than the diameter of the screw head so as to capture the screw in the housing. Also the housing is slightly larger than the bottom opening so that the convexly rounded screw head has some play in the pocket to allow some freedom of angulation (i.e. about 5 to about 30°, preferably about 10 to about 20°) of conical or modified conical rotational freedom of the screw relative to the housing axis (as measured from the groove formed through the compression opening.) The angle of the axis of the oblique screw is from about 10° to about 70°, more specifically about 25° to about 60° and most specifically about 35° to about 55° degrees to a longitudinal axis of the plate which dissects the compression opening on the plate (i.e. the "spine of the plate"). A compressive force is applied to the bone by the plate as the oblique screw is screwed tighter and the screw head compresses into an increased fit with the pocket, and in particular with the pocket bottom opening. This draws the bone segment into which the compression screw is screwed toward the locking screw or screw in the other end of the plate.

In the specific embodiments shown, the plate can include and is limited to (i.e. "consists essentially of") a simple tab-like shape with the compression housing at one slightly elongated rounded end of the plate and a locking screw hole with external threads that mate with ah internally threaded hole at the other rounded end of the plate where the plate profile or outline does not include other projections, but is limited to a first end and second end, with a first end having the bottom compression pocket with the first end opposing a second end with a second hole including internal locking threads, and the plate outline defining an longitudinal axis about which the plate is symmetrical and along which the compression hole and the locking hole are aligned. In the z plane, the plate can include a continuous curve of the same radius along the length of the longitudinal axis, i.e. to form a portion of a cylinder.

In a second embodiment, of the plate, a more complex and application specific configuration is illustrated as a MTP plate, which is intended to span the MTP joint. In a first version of the MTP plate of the present invention, the plate has (again "consists essentially of") a first end with two lateral tabs on either side of a middle tab, and a second end with two lateral tabs and no intermediate tab. Each of these tabs is provided with a threaded screw hole that receives a threaded locking screw. The end with the two tabs, also includes a compression housing as previously described that accepts a screw which extends toward the first end of the plate with its axis at an oblique angle of about 5° to about 40°, more preferably about 10° to about 30°, and most preferably about 15° to about 25° with respect to the longitudinal axis of the plate. Further, the plate has an angle of up to about 10° (and preferably about 5°) for dorsiflexion and an angle up to about 10° for valgus. The bottom surface of the plate is radiused. This allows the plate to be in snug contact with the bone. This plate is also provided in a second version which differs from the first in that the second end does include three tabs similar to the first end, an the compression housing is located at an oblique angle of about 5° to about 40°, more preferably about 10° to about 30°, and most preferably about 15° to about 25° to the lateral side of the plate and intermediate along the longitudinal axis to the tabs, and further houses a screw hole that defines an axis at an angle of about 55°, /–about 15°, preferably about 10°, and most preferably about 5° to a line perpendicular to the plate surface at a point along the plate longitudinal axis. The compression housing is similar in concept to the previously described compression housing, but in this case, has a round footprint describing at least a portion of a circle, and preferably is substantially a portion of a circle, with a leading edge that is linear. Once again, the housing has an internal recess that houses the compression screw and which has a narrowed opening, that is smaller than an associated screw head so as to capture and retain the screw, but which allow for conical rotation in the compression housing.

In a third embodiment, the plate is a bunionectomy plate, which includes (and which "consists of" or "consists essentially of") a first end with symmetrical lateral tabs (i.e. mouse ears) and a second tapered end with a deep chamfer for insertion into bone. The tabs include threaded locking holes for threaded locking screws. The plate, includes the compression pocket (described above) and screw spaced from, but at the same end (that is more or less in the middle of the plate) as the double lateral tabs. The pocket receives and captures a rounded headed screw, which extends obliquely toward the chamfered end of the plate. This plate is planar on the top side and the bottom side, except for the protruding housing on the bottom side.

The invention also relates to a novel surgical procedure, which is a bunionectomy that involves the use of the bunionectomy plate of the present invention.

BRIEF DESCRIPTION OF THE DRAWINGS

FIG. 31 is a top view of a second version of the embodiment of the plate shown in FIG. 7;

FIG. 32 is a first side view of the plate shown in FIG. 31;

FIG. 33 is a cross-section of the plate shown in FIG. 31 taken along line 33-33;

FIG. 34 is a bottom view of the plate shown in FIG. 31;

FIG. 35 is a cross-section of the plate shown in FIG. 31 taken at line 35-35;

FIG. 36 is a top view of a third version of the embodiment of the plate shown in FIG. 7; and FIG. 37 is a detail in cross section of the plate shown in FIG. 31.

DETAILED DESCRIPTION OF THE INVENTION

Figure 1:
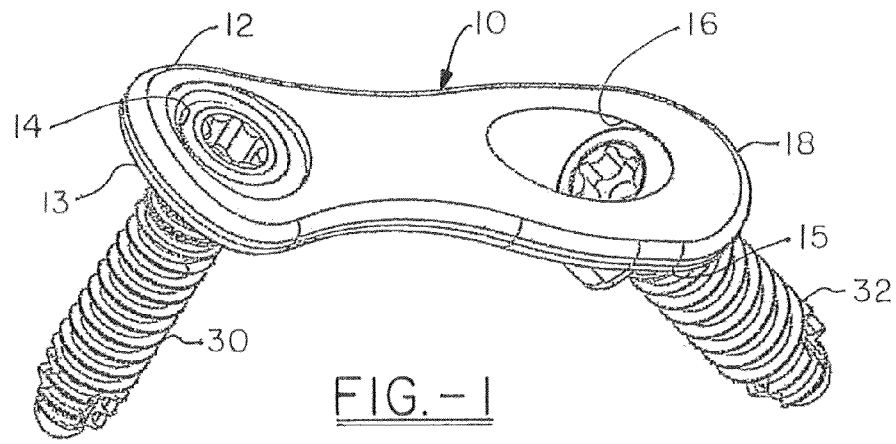
FIG. 1 is a top perspective view of the orthopedic compression plate in accordance with the present invention.
Figure 2:
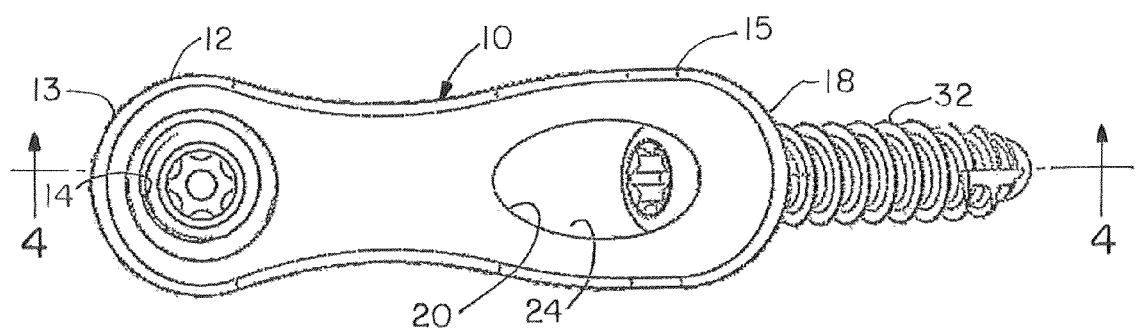
FIG. 2 is a top view of the orthopedic plate of FIG. 1.
Figure 3:
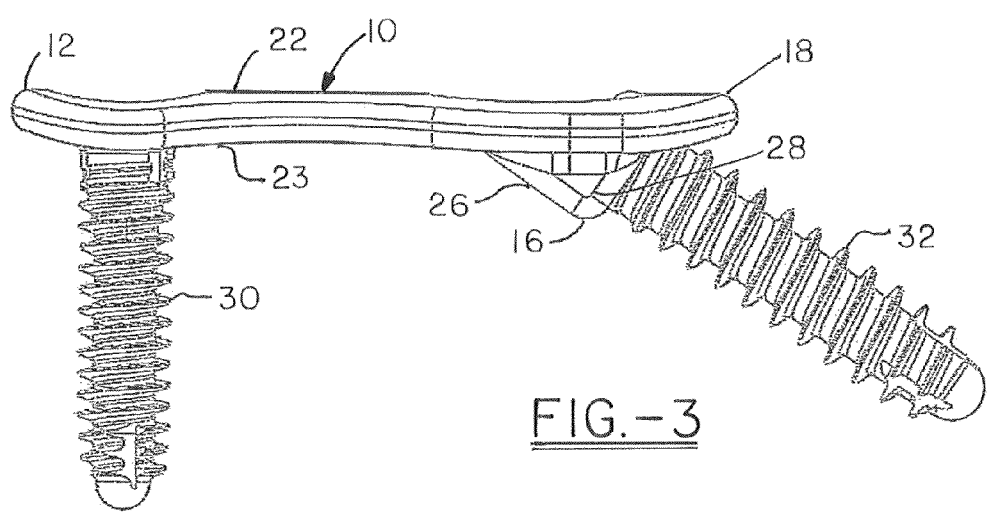
FIG. 3 is a first side view of the plate shown in FIG. 1.
Figure 4:
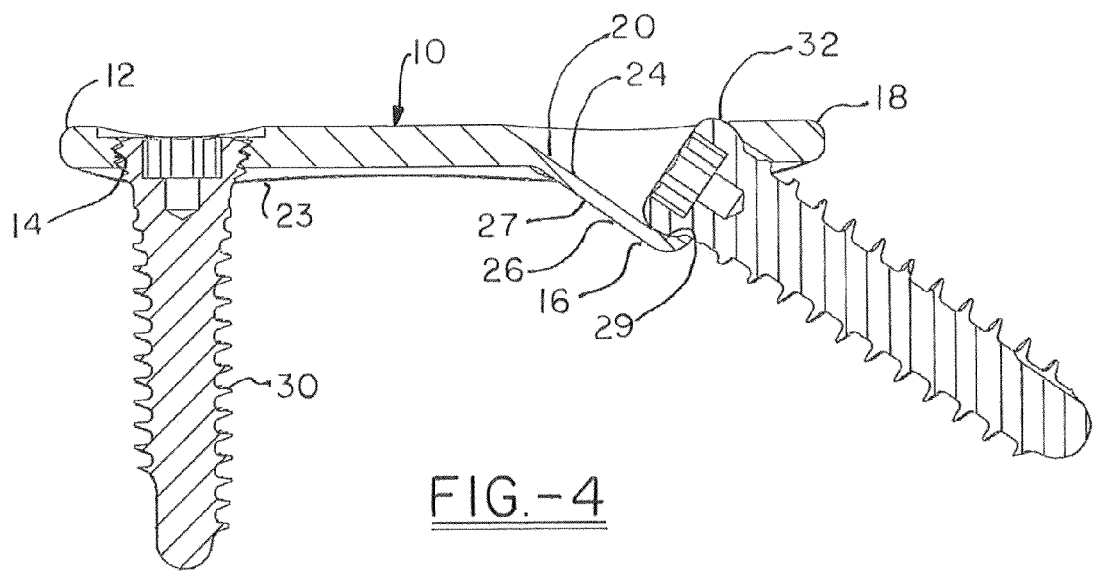
FIG. 4 is a first cross-sectional view of the plate shown in FIG. 1, taken along line 4-4.
Figures 5, 6:
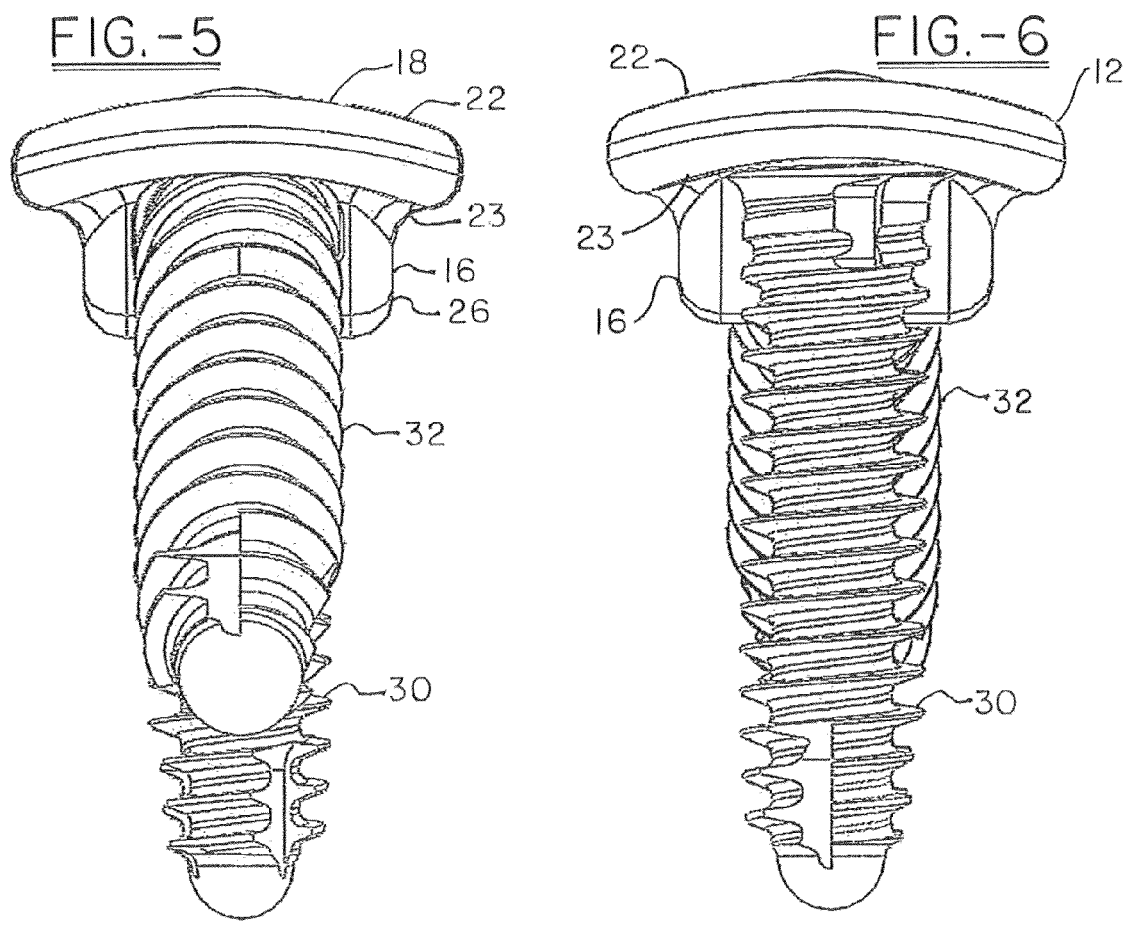
FIG. 5 is a right end view of the plate shown in FIG. 1.
FIG. 6 is a left end view of the plate shown in FIG. 1.

FIGS. 1-6 show a first embodiment of the compression pocket plate of the present invention. This embodiment illustrates the compression housing of the present invention used with a universal two ended plate 10 which can be used for a variety of applications in which it is desirable to achieve compression for a relatively small area between bones or bone fragments. The plate has a first end 12 having a rounded tab 13 just large enough to form a suitable mounting for a threaded locking hole 14, which receives a threaded locking screw 30. As used herein the term "tab" suggests a projection which includes a rounded portion for example large enough to accommodate an opening for a screw hole and contiguous material which holds the rounded projection to the general plate body. The plate also has a second end 18 with an elongated tab 15 that includes a compression housing 16. The compression housing 16 includes an opening 20 in the top surface 22 of the plate. The opening 20 is ovoid, with a width that wide enough to accept the compression screw 32 that is received in the opening 20. The opening 20 angles into the top surface 22 of the plate 10 so as to form a groove 24 that accommodates and guides the screw 32 and a mating driver as the screw is screwed into the bone below the plate. On the bottom surface 23 of the plate 10 there is a shroud 26, which has a rectangular flat rear surface 27 joined to flat side walls 28. The shroud 26 includes a lower opening 29 which is circular, and which is large enough to allow the major diameter of the screw to pass through, but which is smaller than the diameter of the rounded portion 34 of the head of the screw 32.

Figure 7:
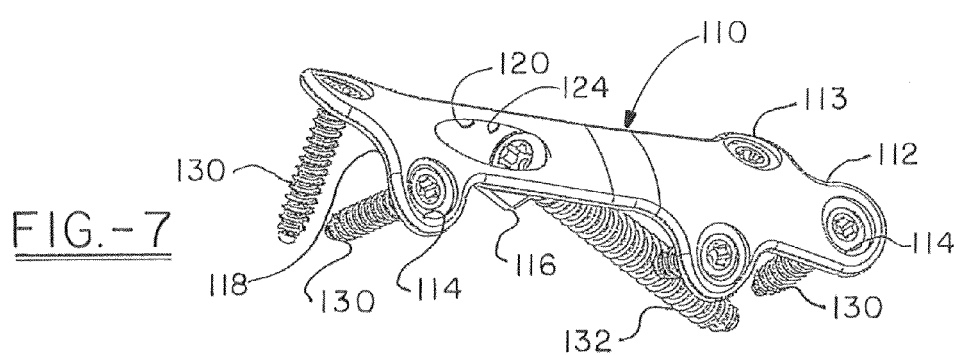
FIG. 7 is a top perspective view of second embodiment of the orthopedic compression plate in accordance with the present invention.
Figure 8:
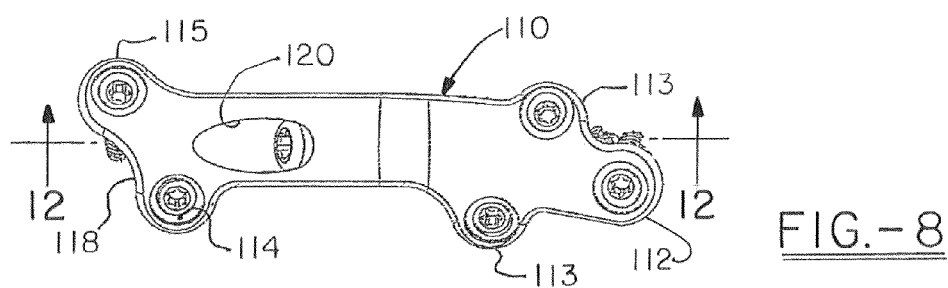
FIG. 8 is a top view of the orthopedic plate of FIG. 7.
Figure 9:
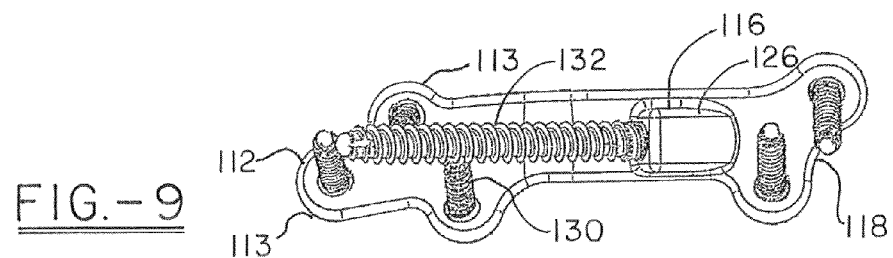
FIG. 9 is a bottom view of the orthopedic plate of FIG. 7.
Figure 10:
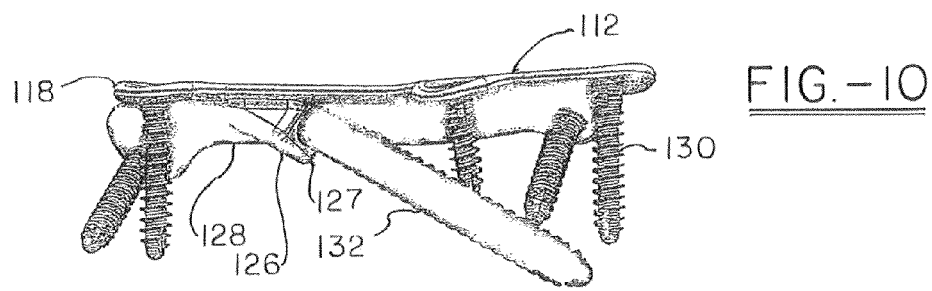
FIG. 10 is aside and bottom perspective view of the plate of FIG. 7.
Figure 11:
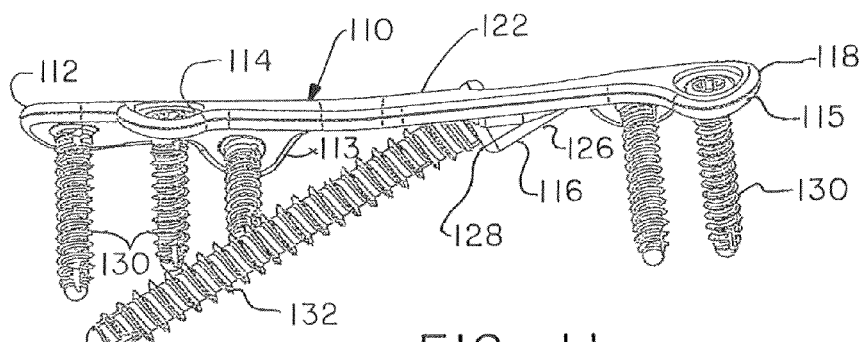
FIG. 11 is a first side view of the plate shown in FIG. 7.
Figure 12:
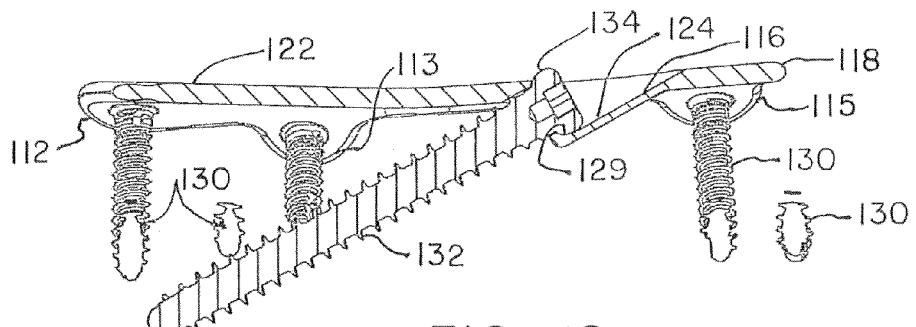
FIG. 12 is a first cross-sectional view of the plate shown in FIG. 8, taken along line 12-12.
Figure 13:
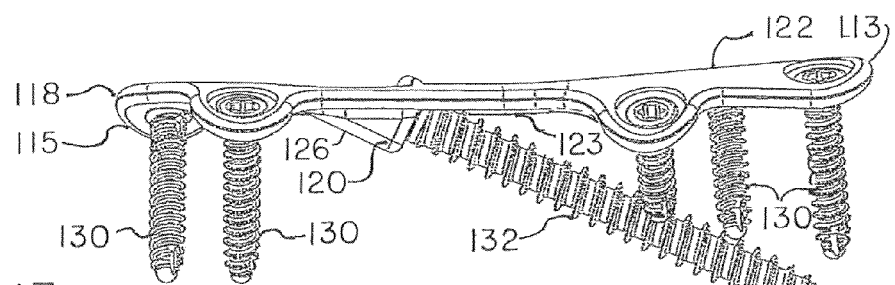
FIG. 13 is a side view taken from the other side of the plate shown in FIG. 7.
Figure 14:
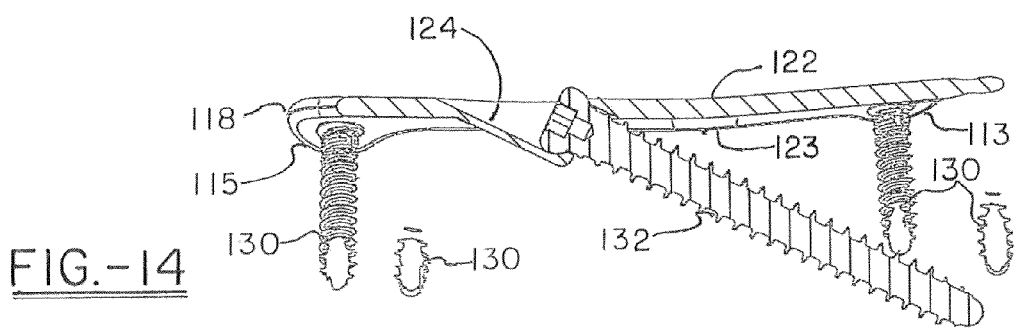
FIG. 14 is a second cross-sectional view of the plate shown in FIG. 8, taken along line 12-12 and looking in the opposite direction from FIG. 12.
Figure 15:
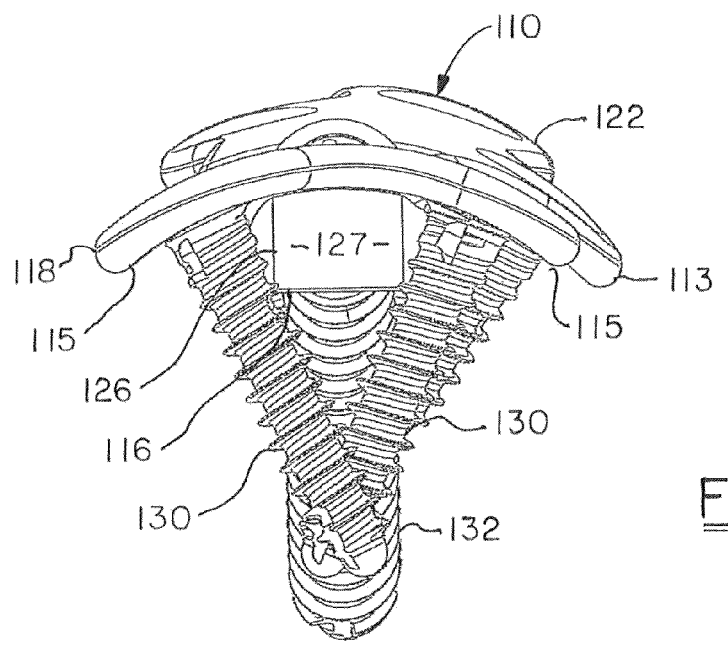
FIG. 15 is a left end view of the plate shown in FIG. 7.
Figure 16:
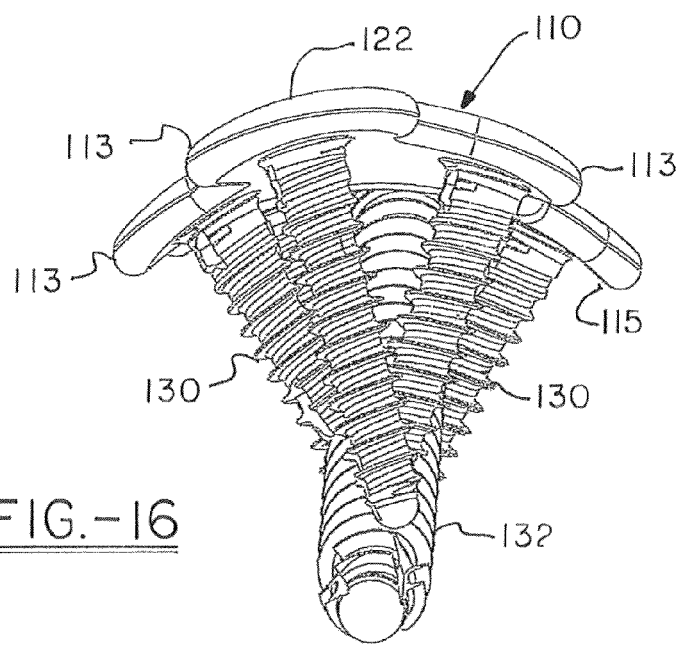
FIG. 16 is a right end view of the plate shown in FIG. 7.

FIGS. 7-16 show a first version of an application specific plate which is for use in the MTP joint, the junction of the head of the first metatarsal and the proximal phalange of the first ray (i.e. the great toe) at the first metatarsophalangeal joint. The plate used in fixation (i.e. for fusion) of the bones of the first MTP joint, and is thus termed an MTP plate. The plate 110 has a first end 112 which is tri-lobed, or has three rounds tabs 113, of just appropriate size to form mounting rings for threaded locking holes 114 which receive threaded locking screws 130. The tabs are longitudinally offset from each other, and angled inward toward the medial axis of the plate to improve the purchase in the plate, and inhibit backout. The other end 118 of the plate 110 includes two laterally and longitudinally offset tabs 115 which are also just of appropriate size to form mounting rings for threaded locking holes 114 which receive threaded locking screws 130. The second end 118 of the plate includes a compression housing similar 116 to that described for the universal plate. The compression housing 116 includes an opening 120 in the top surface 122 of the plate. The opening 120 is ovoid, with a Width that wide enough to accept the compression screw 132 that is received in the opening 120. The compression screw is of slightly greater diameter and of greater length than the locking screws. The opening 120 angles into the top surface 122 of the plate 110 so as to form a groove 124 that accommodates and guides the screw 132 and a mating driver as the screw is screwed into the bone below the plate. On the bottom surface 123 of the plate 110 there is a shroud 126 which has a rectangular flat rear surface 127 joined to flat side walls 128. The shroud 126 includes a lower opening 129 which is circular, and which is large enough to allow the major diameter of the screw to pass through, but which is smaller than the diameter of the rounded portion 134 of the head of the screw 132. The end 118 with the two tabs 115, also includes a compression housing 126 as previously described that accepts a screw 132 which extends toward the first end 112 of the plate with its axis at an oblique angle of about 5° to about 40°, more preferably about 10° to about 30°, and most preferably about 15° to about 25° with respect to the longitudinal spine of the plate. Further, the plate has an angle of up to about 10° (and preferably about 5°) for dorsiflexion and an angle up to about 10° for valgus. The bottom surface of the plate is radiused at a constant curve.

Figure 17:
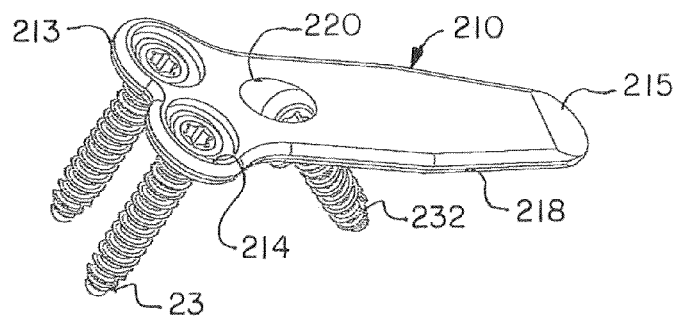
FIG. 17 is top perspective view of a further embodiment of an orthopedic pocket compression plate in accordance with the invention.
Figure 18:
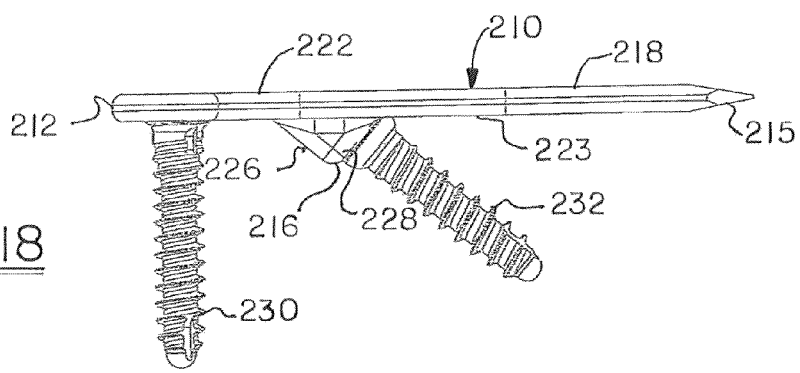
FIG. 18 is a first side view of the plate shown in FIG. 17.
Figure 19:
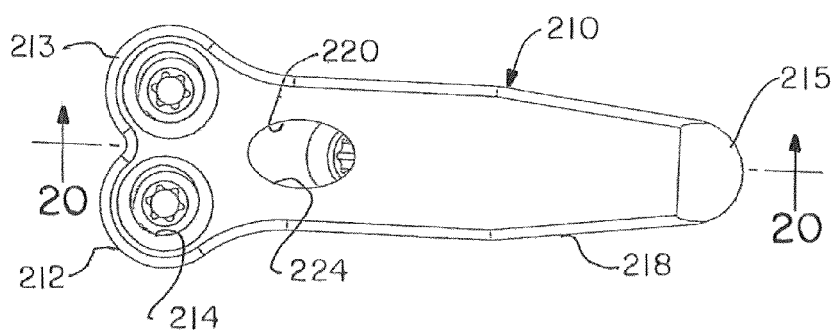
FIG. 19 is a top view of the plate shown in FIG. 17.
Figure 20:
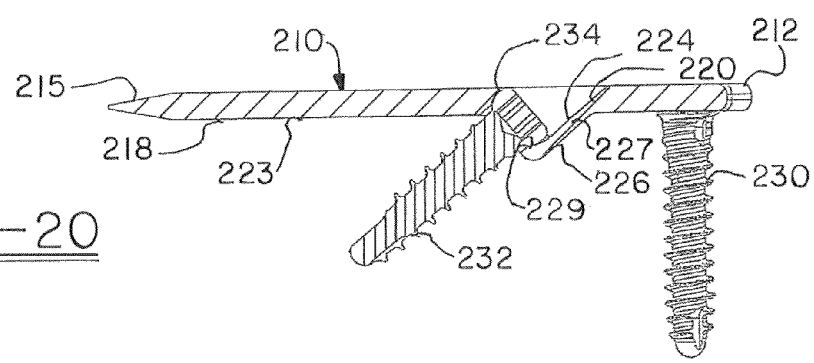
FIG. 20 is a first cross-sectional view of the plate shown in FIG. 17, taken along line 20-20.
Figure 21:
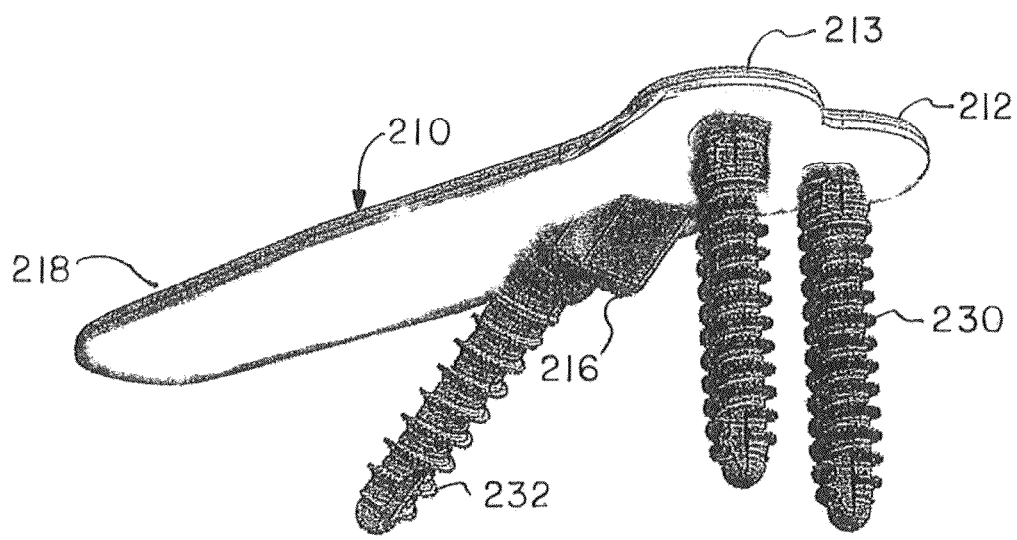
FIG. 21 is a side and bottom perspective view of the plate of FIG. 17.
Figure 22:
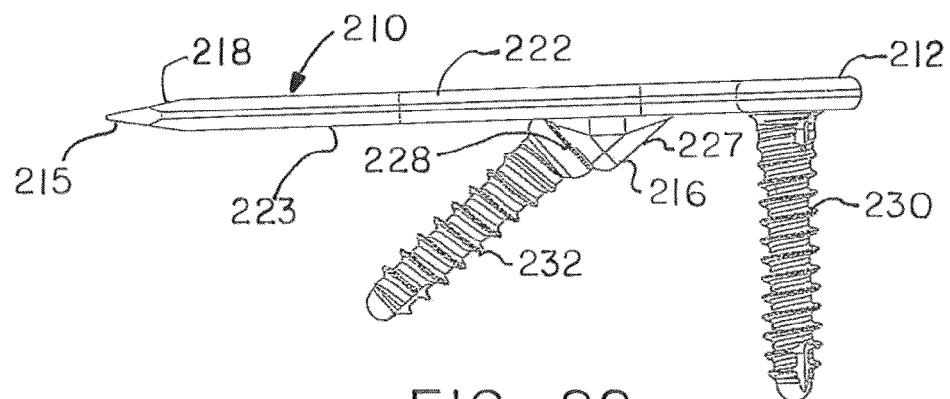
FIG. 22 is a side view, of the plate of FIG. 17.
Figure 23:
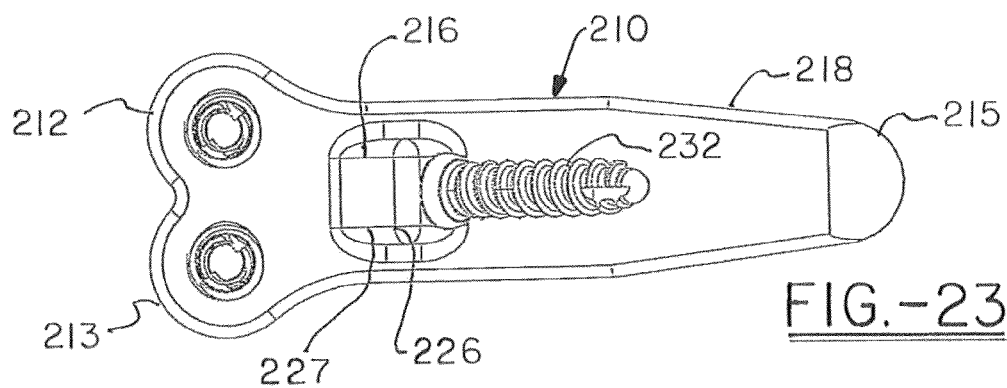
FIG. 23 is a bottom view of the plate of FIG. 17.
Figure 24:
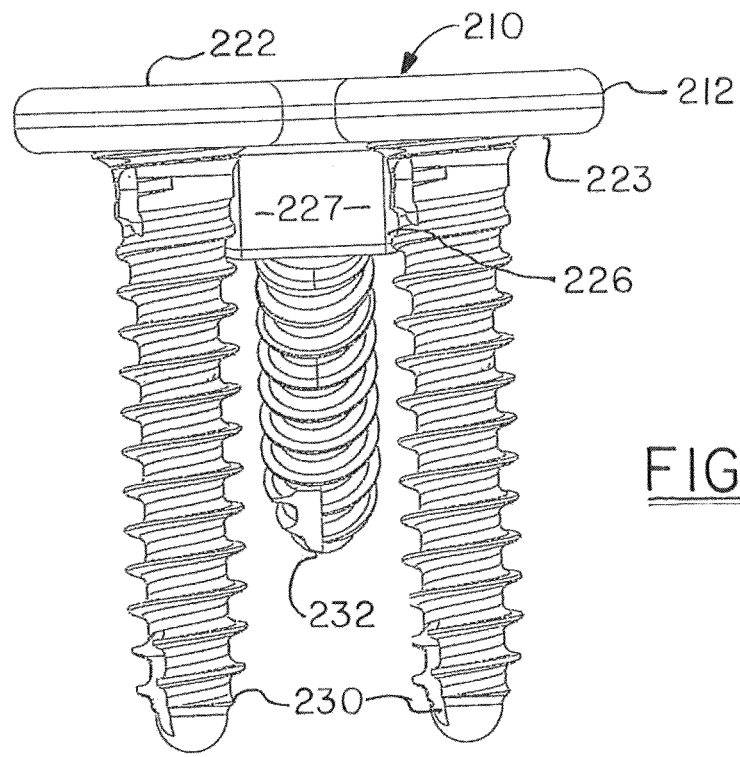
FIG. 24 is a left end view of the plate of FIG. 17.
Figure 25:
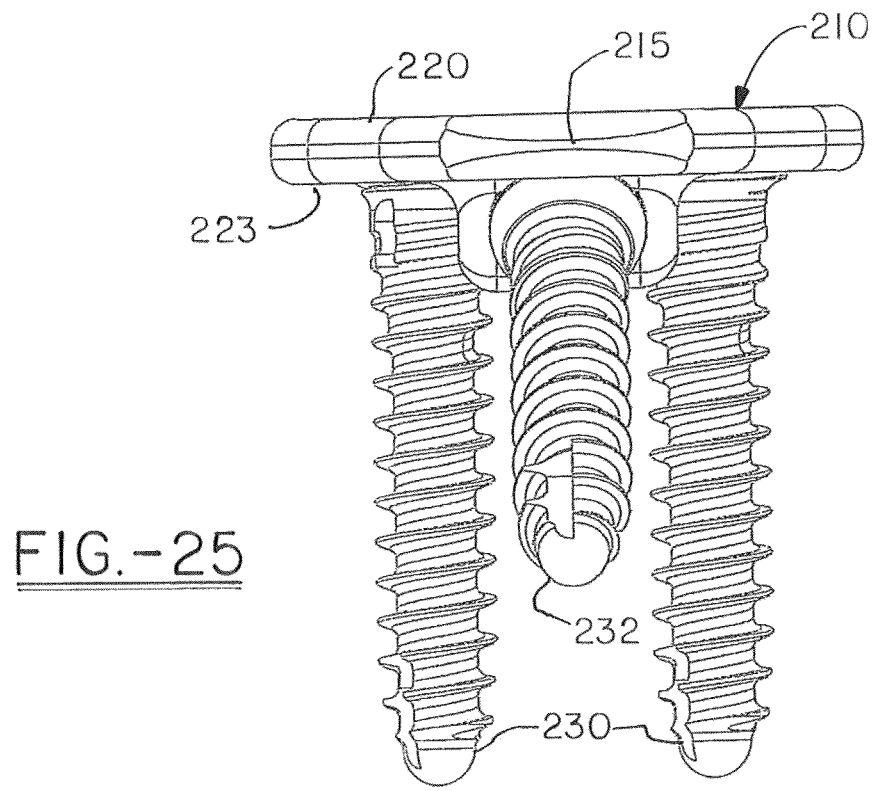
FIG. 25 is a right end view of the plate of FIG. 17.
Figure 26:
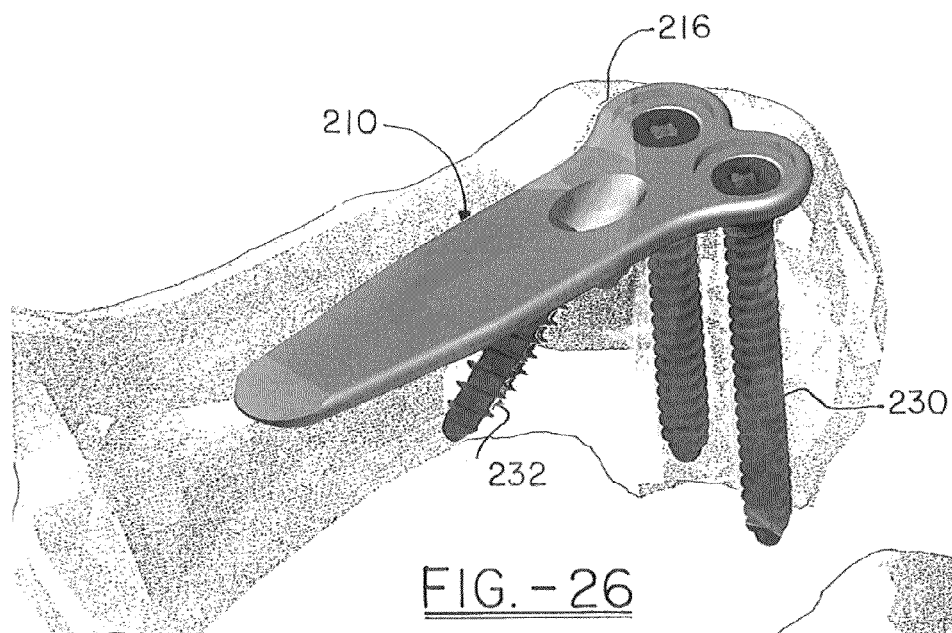
FIG. 26 is a view the plate of FIG. 17 on the first metatarsal after bunionectomy surgery.
Figure 27:
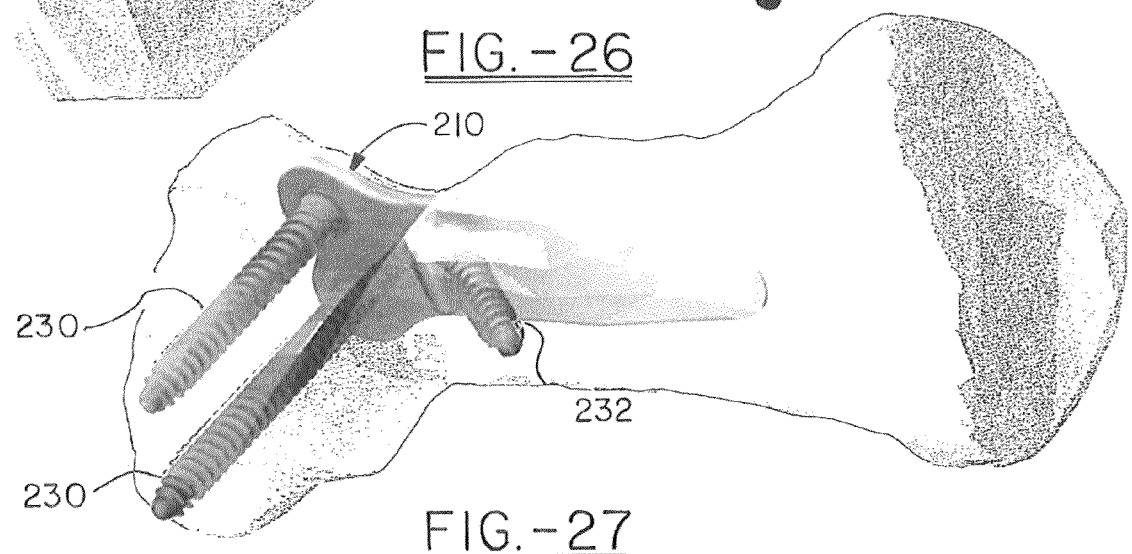
FIG. 27 is a view of the plate and bone shown in FIG. 26 from the top and lateral side of the bone.
Figure 28:
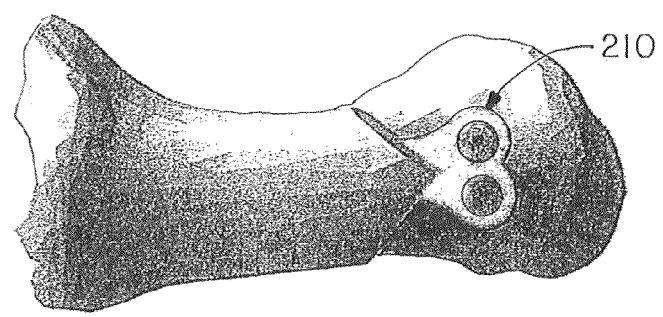
FIG. 28 is a view of the bone and plate of FIG. 26 taken from the medial side of the body.
Figure 29:
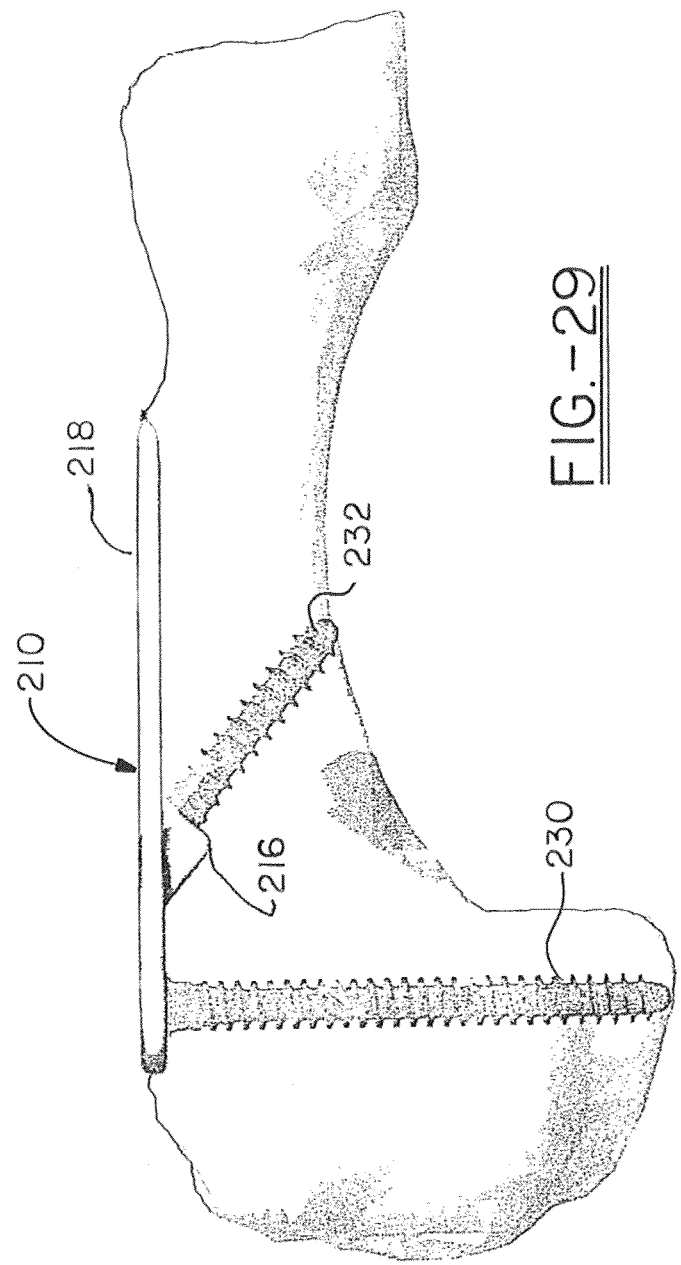
FIG. 29 is a view of the bone and plate of FIG. 26 taken from the bottom side of the bone.
Figure 30:
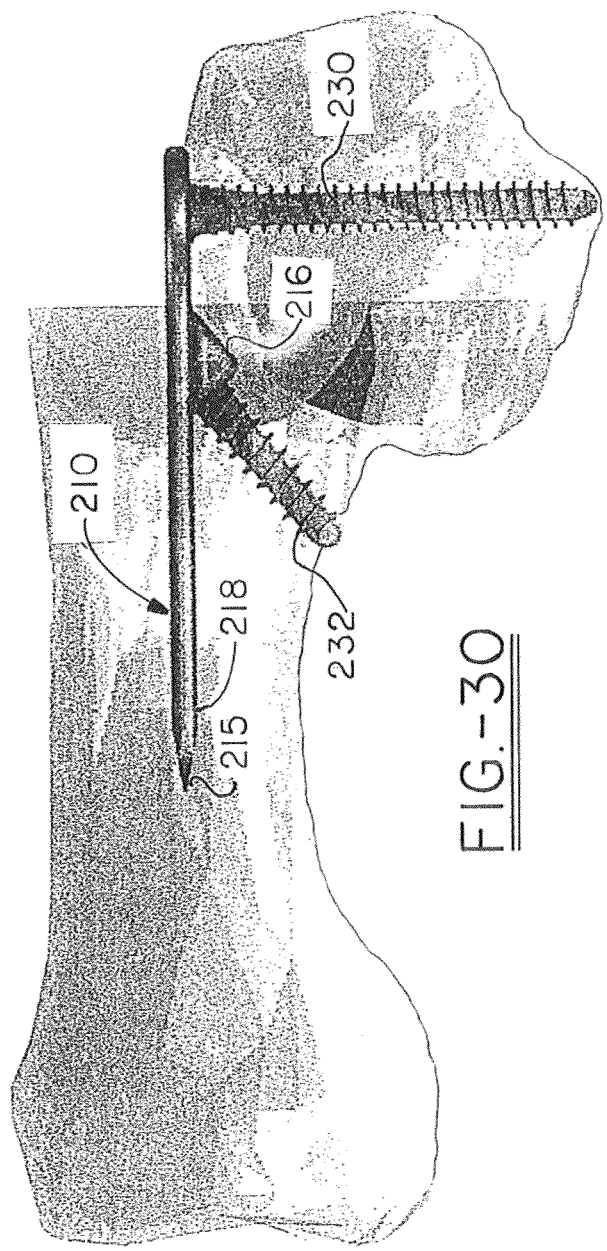
FIG. 30 is a view of the bone and plate of FIG. 26 taken from the top side of the bone.

A third embodiment of the plate is shown in FIGS. 17-30. In this version, the plate is intended for a bunionectomy. The plate 210 has a first end 212 having symmetrical double rounded tabs 213 (i.e. mouse ears) just large enough to form a suitable mounting for threaded locking holes 214, which receive a threaded locking screws 230. The also has a second end 218 with an elongated tab 215 that tapers and includes a sharp chamfer, suitable for insertion into bone, such as by tamping. The plate also includes a compression housing 216. The compression housing 216 includes an opening 220 in the top surface 222 of the plate. The opening 220 is ovoid, with a width that wide enough to accept the compression screw 32 that is received in the opening 220. The opening 220 angles into the top surface 222 of the plate 210 so as to form a groove 224 that accommodates and guides the screw 232 and a mating driver as the screw is screwed into the bone below the plate. On the bottom surface 223 of the plate 210 there is a shroud 226, which has a rectangular flat rear surface 227 joined to flat side walls 228. The shroud 226 includes a lower opening 229 which is circular, and which is large enough to allow the major diameter of the screw to pass through, but which is smaller than the diameter of the rounded portion 234 of the head of the screw 232.

FIGS. 31-35 illustrate a second version of the second embodiment, i.e. the MPT plate 310, of the present invention. In this version both the first and the second ends 312,318 includes three tabs 313,315 and locking holes 314 within each tab. The plate 310 continues to have the same angles for dorsiflexion and for valgus. In the first end, in which an axis can be defined along the medial axis of the plate to the midline, and dividing the terminal most screw hole in half, the second tab hole forms an angle of about 25° to the long axis and the screw hole has an angle of about 21°+/−8°, preferably +/− about 5°, and most preferably about 2° to the screw axis of the terminal most hole, while the screw hole in the third tab has an angle of about 18°+/−8°, preferably +/− about 5°, and most preferably about 2° to the screw axis of the terminal most hole, with a preferred difference of about 3°. The geometry of the opposite end of the plate mirrors the first end, with the exception that the second end further includes a tab 317 for a compression shroud 316 which extends from the bottom surface of the plate and intermediate to the second tab and has a screw housing that extends from the bottom of the plate at an angle of about 55°+/−about 10°, preferably about 8°, and most preferably about 5° relative to the screw hole axis of the terminal most screw hole. The housing has a cylindrical configuration, which intersects the plate at a linear edge. The housing has a narrowed opening that acts to capture a screw housed in the housing but which allows conical rotation in the housing. The inside wall of the housing narrows at an angle of 40° relative to the axis of the housing. The housing 316 has a narrowed opening that acts to capture a screw housed in the housing but which allows conical rotation in the housing. The inside wall of the housing narrows at an angle of 40° relative to the axis of the housing. On the bottom surface 323 of the plate 310 there is a shroud 316, which has a rear surface 327 joined to side walls 328. The shroud 316 includes a lower opening 329 which is circular, and which is large enough to allow the major diameter of the screw to pass through, but which is smaller than the diameter of the rounded portion 234 of the head of the screw 232.

FIG. 36 illustrates a third version of the second embodiment, i.e. the MPT plate 410, of the present invention, which is a mirror image of the plate shown in FIGS. 31-37. Once again, both the first and the second ends 412,418 includes three tabs and locking holes 414 within each tab and t the second end also includes a tab 417 for a compression shroud 416 which extends from the bottom surface of the plate. The plate continues to have the same angles for dorsiflexion and for valgus. The geometry of the opposite end of the plate mirrors the first end, with the exception that the second end further includes a fourth tab intermediate to the second tab and has a screw housing that extends from the bottom of the plate at an angle of about 55°+/−about 10°, preferably about 8°, and most preferably about 5° relative to the screw hole axis of the terminal most screw hole. The housing has a cylindrical configuration, which intersects the plate at a linear edge.

In one method of causing locking of the screw relative to the plate, the screw could include external screw threads that mate with internal threads in the locking screw hole at a pre-selected angle, in some instances, the screw axis is perpendicular to a tangent at the top of the screw hole so that the screw axis angles slightly toward the bottom of the plate. However, other methods of pausing locking could be employed, such as a variable locking assembly. The screw used in the compression housing has a rounded rear shoulder (such as a hemisphere, or a torroid), which allows for play in the convexly rounded recess in the compression housing. The compression is caused when the compression screw engages the bone and pulls the plate into that bone, and the locking screw or screws act on their respective bone segment.

The screws useful with the plate of the present invention are self-starting, self-tapping screws including the option of partial or full cannulation. The screws include a cutting end having multiple flutes, and preferably 2 or 3 flutes about a conical recess, and preferably have a rounded end to avoid soft tissue irritation should they break an opposing cortical surface. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.2 and 1.5 millimeters, and most preferably between about 1.25 and 1.40 millimeters. The compression housing extends a depth below the bottom surface of the plate from about 1.4 to about 3 mm, preferably from about 1.75 to about 2.25 mm, and has a width of from about 3.5 to about 5.5, preferably from about 4 to about 5 mm., and a length of from about 3.0 to about 8.0, mm preferably from about 5.0 to about 7.0 mm. The opening in the upper surface of the plate for the compression opening is from about 8 to about 15 mm in width, and from about 10 to about 18 mm in length. The lower opening is about 2.5 to about 2.9 mm in diameter with a recess width of from about 2.5 to about 4.5 mm. The locking screw holes include a flat annular recess surrounding the threaded area that is about 0.4 to about 0.6 mm in width. The universal plate (i.e. the tab-like plate) has a length of from about 35 to about 45 mm, preferably from about 38 to about 42 mm, and the compression screw axis forms an angle of from about 30° to about 40° to a longitudinal axis on the top of the plate. The MTP plate has a length of from about 40 to about 50 mm in length, The compression screw axis forms an angle of about 22° to about 37° with a longitudinal axis tangent to the bottom of the plate at the housing exit. In the bunionectomy plate, the chamfer at the bone insertion end is from about 5° to about 15°, preferably from about 8° to about 12°, and the length of the chamfer is from about 2 to about 4 mm, preferably from about 2.5 to about 3.5 mm and the plate has a total length of from about 175 to about 225 mm, preferably from about 185 to about 200 mm, with the taper. The axis of the compression screw forms an angle of from about 35° to about 45° to a longitudinal axis on the bottom of the plate. The plate includes a continuous outer edge which is defined between the top and the bottom surface. In addition, the plate 10 can include a small through hole 28 sized to receive a K-wire or other similar guide wire.

During the surgery the joints are first prepped which may include de-articulation between the bones to be fused. The bones are reduced, the plate is located such that all of the screws are aimed into the targeted bones and away from the joint, and the locking screw(s) is inserted into a pre-drilled pilot hole or holes. A pilot hole is drilled for the compression screw, and the compression screw is tightened into position. The two locking screws are screwed into adjacent cunieforms. The plate is viewed radiographically. The incision is closed per the usual method.

For the bunionectomy in accordance with the invention, the first metatarsal joints are first prepped which may include de-articulation between the bones to be fused and removal of any bone as part of the osteotomy, and as necessary, the plate is bent to contour to the bone surface. A pilot hole may be drilled into the bone into which the plate will be inserted. The plate is inserted into the plate recess in a plate driver and secured by tightening the plate upward in the plate holder using the plate holder having an end that has threads, which mate with the locking threads of the locking hole in the plate. The plate is tamped into the cancellous portion of the bone fragment optionally by tapping the plate driver with a one pound mallet as is necessary to insert the plate. The plate should be driven until the recess or pocket makes contact with the anterior portion of the calcaneus bone. An area may be cleared on the cortical surface of the area of bone that will receive the section with the locking screws. Once the tapered end of the plate is sunk, a drill guide is mated to the plate drive, and a hole is drilled for the locking screw. The plate can be held in position using olive wires (thru the locking holes and into the bone). The plate is located such that all of the screws are aimed into the targeted bones and away from the joint, fracture, or bone interface. The olive wire is removed if used, and a pilot hole is drilled at the end of the plate that includes the first hole and this hole is pinned or screwed. A second pilot hole may be drilled for the compression screw at the desired angle given an optional 15° of conical rotation within the compression screw hole and a non-locking screw is inserted into this pilot hole and tightened. As the compression screw is tightened in the angled hole, it will drive compression toward the fusion site and the locking holes. The plate is viewed radiographically, and the soft tissues are closed in the usual manner.

The following is a description of a surgical technique for an MTP fusion using the MTP fusion plate in accordance with the present invention. First, prepare the MTP joint for fusion and choose the desired plate from the surgical tray. Note, that the plates are pre-contoured to provide 10° of valgus and 5° of dorsiflexion and can be used on either foot. The plates should, be placed so that the plate's pocket is on the medial side of the foot. For instance, using the Alpha™ plate on the right foot the pocket is on the proximal side of the joint. When used on the left foot, the pocket of the Alpha™ plate is on the distal side of the joint. If necessary, use the bending pliers to contour the plate to the bone surface. Using a k-wire, placed in the plantar portion of the bones from medial to lateral across the joint, temporarily fix the joint in the desired position. Assemble the template that corresponds to the chosen plate with the countersink guide by snapping the template into the guide. Lay the template on the bone and orient to the desire position of the plate. Place two 0.9 mm k-wires. Prepare for the plate pocket and inter-fragmentary screw with the provided countersink through the template assembly. Insert the countersink until the shoulder of the countersink hits the guide normal to the plate in the k-wire holes. With the k-wires still in place, slide the template off the bone and using the wires to help placement, slide the chosen plate over the k-wires so that the plate's pocket fits within the prepared hole. Select one of a fixed locking, non-locking or variable angle locking screw to be used in one of the threaded locking holes that is on the same side of the joint proximally or distally, as the pocket and chose the appropriate drill bit based on the screw selection. Using a color-coded drill guide, drill to the desired depth, determine the screw length using the depth gages, and insert a selected screw into the hole and drive the screw for each screw hole. Using the 1.4 mm guide wire tip, insert a 1.4 mm guide wire in to the pocket hole across the MTP joint and ensure that the guide tip is seated within the pocket before inserting the wire. Use the cannulated drill bit to drill for the inter-fragmentary pocket screw over the guide wire. Determine the required screw length over the guide wire using the depth gage and insert the inter-fragmentary screw in the pocket of the plate using the corresponding driver. Before the pocket screw is completely seated, remove the k-wire used for temporary fixation and fully tighten the pocket screw. Fill all remaining screw holes and completely tighten all remaining screws. Verify the correct placement of the plate and screws, replace soft tissue and close the opening.

In the intraosseous version of the present invention, the plate combines the bending strength and rotational control of a plate with the compression generation of an inter-fragmentary screw and also provides the advantage of allowing the placement of an inter-fragmentary screw through a plate, using the plate to lock the construct in place to achieve optimal compression. This plate uses the axis of the pocket to direct the fixation screw into the proximal metatarsal. This indication specific plate and accompanying instrumentation will aid in increasing surgeon accuracy in screw placement. For larger corrections requiring significant displacement of the metatarsal head, the set has an intramedullary plate option, to improve the overall construct stability. The custom bone prep instrumentation and the bottom-side pocket create a low profile construct with no exposed screw heads to cause soft-tissue irritation Below is an example of a surgical technique of the use of the intraosseous plate having a compression shroud in accordance with the invention.

First, perform a standard medial approach for the first metatarsal phalangeal joint, and then, using a microsagittal saw, remove the medial eminence, on the distal head of the first metatarsal and make a distal, transverse V-shaped osteotomy (i.e. Chevron) or other translational type osteotomy through the first metatarsal at least 10 mm from the articular surface. The cut should be made from medial to lateral. Shift the distal head of the metatarsal laterally until the desired intermetatarsal angle is achieved. If desired, a k-wire may be used to provisionally fix the osteotomy. Once the desired shift is achieved, place the broach against the flat, cut surface of the metatarsal head. Taking care as to the placement of the broach into the metatarsal parallel to the medial border of the foot, push the tip of the broach into the proximal metatarsal shaft until the broach contacts the osteotomy site, making sure to keep the broach parallel to the medial border of the foot. If necessary, a mallet can be used to gently tap the broach into place. Insert the countersink into the ratcheting handle and through the hole in the broach. Drill with the countersink until the shoulder on the countersink hits the top surface of the broach and remove the countersink. With the broach still in place, use the microsagittal saw to re-sect the residual (overhanging) proximal metatarsal shaft and remove the broach.

Select the intraosseous plate from the surgical tray and cautiously insert the proximal end of the plate into the plate driver and rotate the driver insert clockwise until the plate rests securely in the drive pocket. Once the plate is attached to the driver, push the sharp end of the plate into the slot prepared by the broach. If necessary, a mallet can be used to gently tap the back of the driver until the driver makes contact with the distal-most portion of the osteotomy on the proximal bone. Once the plate is properly positioned, the 1.6 mm drill bit is inserted through the driver insert to drill a hole for the 2.4 mm fixed angle locking screw. After the hole has been drilled, the insert is unscrewed from the plate and the driver and mating insert is removed. The fixed angle locking screw length is determined using the provided depth gage and the screw is inserted. The 1.6 mm fixed drill guide is selected, threaded into the other distal locking hole that has not been drilled and a pilot hole of the desired depth is drilled. Both locking screws are fully tightened. The pocket drill guide is attached to the drill guide handle and inserted to the desired depth with the guide fully seated and oriented so that the trajectory of the drill is as steep as possible in order to help prevent skiving of the drill bit off the inner surface of the lateral cortex. The depth gage is used to determine the 2.4 mm non-locking screw length; the selected screw is inserted and tightened until sufficient compression across the osteotomy is achieved. The plate and screw placement is verified using fluoroscopy. Soft tissues are repaired as needed and the incision is closed as desired.

While in accordance with the patent statutes the best mode and preferred embodiment have been set forth, the scope of the invention is not limited thereto, but rather by the scope of the attached claims.

What is claimed is:

1. A plate and screw system which is capable of fixation of bone comprising a plate and a locking screw and a compression screw, the compression screw having a convexly rounded head having a diameter, the plate having a top surface opposing a bone facing surface in the z direction, and extending along a first length along a longitudinal axis and having a first end and a second end, and the plate including a compression screw housing which extends through the plate to form a pocket extending from the bone facing surface of the plate and defining a compression screw hole extending along a compression screw hole axis to define a compression screw angle of from 10° to 70° in the Z direction relative to the longitudinal axis of the plate and the compression screw housing including a ovoid opening in the top surface of the plate which opens to the pocket which has rear and side walls extending from the bone facing surface of the plate and away from the top surface of the plate and which define inside surfaces of the pocket and the inside surfaces of the pocket defining the ovoid opening at the plate top surface which opens into the pocket at an angle to form a groove that accommodates and guides the screw and a mating screw driver as the screw is screwed into a bone, the pocket having a bottom opening on the bottom of the plate, and that is smaller than the diameter of the compression screw head, the inside surfaces of the pocket being of a sufficient size to accommodate the entire screw head whereby the compression screw is captured in the pocket and can be positioned at a variable angle relative to the compression screw hole axis and the screw head does not project beyond the top surface of the plate, and the second end of the plate further includes a chamfer for insertion into bone.

2. The plate and screw system as set forth in claim 1, wherein the compression screw angle is from 20° to 60° relative to the longitudinal axis in the z direction.

3. The plate and screw system as set forth in claim 1, wherein the second end of the plate defines a tab and the plates defines an outline consisting essentially of the first end and the second end.

4. The plate and screw system as set forth in claim 3, wherein the first end defines a second tab which is longitudinally aligned with the second end so as to provide for bilateral mirror symmetry about the longitudinal axis.

5. The plate and a screw system as set forth in claim 1, wherein the first end has two tabs which include locking holes.

6. The plate and a screw system as set forth in claim 5, wherein the first end has three tabs which each include a locking hole, and the second end has two holes which each include a locking hole, and the compression screw housing is located intermediate the first end and the second end.

7. The plate and a screw system as set forth in claim 5, wherein the first end has three tabs which each include a locking hole and the second end has three tabs which each include a locking hole and the second end further includes a fourth tab which includes the compression hole.

8. The plate and screw system as set forth in claim 1, wherein the plate is a MTP plate.

9. The plate and a screw system as set forth in claim 1, wherein the first end of the plate includes a set of two tabs which exhibit bilateral mirror symmetry about the longitudinal axis of the plate and each of the two tabs includes a locking hole.

10. The plate and a screw system as set forth in claim 9, wherein the plate top surface is planar.

11. The plate and a screw system as set forth in claim 1, wherein the plate bone facing surface includes a curve in the z direction.

12. A method of fusing bones, comprising:
surgically accessing a bone,
selecting a plate and screw system comprising a plate and a locking screw and a compression screw, the compression screw having a convexly rounded head having a diameter, the plate having a top surface opposing a bone facing surface in the z direction, and extending along a first length along a longitudinal axis and having a first end and a second end, and the plate including a compression screw housing which extends through the plate to form a pocket extending from the bone facing surface of the plate and defining a compression screw hole extending along a compression screw hole axis to define a compression screw angle of from 10° to 70° in the Z direction relative to the longitudinal axis of the plate and the compression screw housing including a ovoid opening in the top surface of the plate which opens to the pocket which has rear and side walls extending from the bone facing surface of the plate and away from the top surface of the plate and which define inside surfaces of the pocket and the inside surfaces of the pocket defining the ovoid opening at the plate top surface which opens into the pocket at an angle to form a groove that accommodates and guides the screw and a mating screw driver as the screw is screwed into a bone, the pocket having a bottom opening on the bottom of the plate, and that is smaller than the diameter of the compression screw head, the inside surfaces of the pocket being of a sufficient size to accommodate the entire screw head whereby the compression screw is captured in the pocket and can be positioned at a variable angle relative to the compression screw hole axis and the screw head does not project beyond the top surface of the plate, and the second end of the plate further includes a chamfer for insertion into bone,
    fixing a locking screw in the locking hole such that the external threads of the locking screw head mate with the internal threads of the locking screw hole;
    fixing a compression screw in the compression housing to cause compression in the associated bone toward the locking hole.

13. The method of fusing bone as set forth in claim 12, wherein the method involves a surgical procedure which is a bunionectomy.

14. The plate and screw system as set forth in claim 1, wherein the pocket has a bottom opening on the bottom of the plate, and through which the compression screw extends and the pocket and the bottom opening being configured to allow the compression screw to achieve conical rotation with respect to the compression screw axis.

15. A plate and screw system as set forth in claim 1, wherein the plate includes a compression housing which extends through the plate to form a pocket of a sufficient size to accommodate the entire compression screw head.

16. The orthopedic plate and screw as set forth in claim 14, wherein the plate exhibits bilateral symmetry about the longitudinal axis.

17. The orthopedic plate as set forth in claim 15, wherein the locking screw is capable of variable angle relative to the axis of the screw hole.

* * * * *